US008600131B2

(12) United States Patent
Miller et al.

(10) Patent No.: US 8,600,131 B2
(45) Date of Patent: Dec. 3, 2013

(54) ADVANCED COST FUNCTIONS FOR IMAGE REGISTRATION FOR AUTOMATED IMAGE ANALYSIS: MULTI-CHANNEL, HYPERTEMPLATE AND ATLAS WITH BUILT-IN VARIABILITY (75) Inventors: Michael I. Miller, Towson, MD (US); Susumu Mori, Ellicott City, MD (US); Anqi Qiu, Singapore (SG); Jiangyang Zhang, Baltimore, MD (US); Can Ceritoglu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 273 days.

(21) Appl. No.: 12/999,721

(22) PCT Filed: Jul. 7, 2009

(86) PCT No.: PCT/US2009/049812
§ 371 (c)(1),
(2), (4) Date: Dec. 17, 2010

(87) PCT Pub. No.: WO2010/005969
PCT Pub. Date: Jan. 14, 2010

(65) Prior Publication Data
US 2011/0103672 A1 May 5, 2011

Related U.S. Application Data (60) Provisional application No. 61/134,178, filed on Jul. 7, 2008.

(51) Int. Cl.
*G06K 9/00* (2006.01)
(52) U.S. Cl.
USPC .............................. 382/128; 128/922; 378/4

(58) Field of Classification Search
USPC ................ 382/100, 128, 129, 130, 131, 132; 128/922; 378/4–27
See application file for complete search history.

(56) References Cited

U.S. PATENT DOCUMENTS

| 5,970,182 | A  | * | 10/1999 | Goris ........................... 382/278 |
| 6,611,630 | B1 | * | 8/2003  | Miller et al. .................. 382/293 |
| 6,904,161 | B1 | * | 6/2005  | Becker et al. ................. 382/128 |
| 7,428,323 | B2 | * | 9/2008  | Hillman ........................ 382/128 |
| 7,522,744 | B2 | * | 4/2009  | Bai et al. ...................... 382/100 |

(Continued)

OTHER PUBLICATIONS

Miller et al., "Inhibition of rate of tumor growth by creatine and cyclocreatine," Proc. Natl. Acad. Sci., 1993 90, 3304-3308.

(Continued)

*Primary Examiner* — Anand Bhatnagar
(74) *Attorney, Agent, or Firm* — Venable LLP; Henry J. Daley (57) ABSTRACT

A non-invasive imaging system, comprising: an imaging scanner; a signal processing system in communication with the imaging scanner to receive an imaging signal from the imaging scanner; and a data storage unit in communication with the signal processing system, wherein the data storage unit stores template data corresponding to a tissue region of a subject under observation, wherein the signal processing system is adapted to compute, using the imaging signal and the template data, refined template data corresponding to the tissue region, and wherein the refined template data incorporates subpopulation variability information associated with the tissue region such that the signal processing system provides an image of the tissue region in which a substructure is automatically identified taking into account the subpopulation variability information.

31 Claims, 7 Drawing Sheets (56) References Cited

U.S. PATENT DOCUMENTS

| | | | |
|---|---|---|---|
| 7,787,671 B2* | 8/2010 | De Leon et al. | 382/128 |
| 8,199,988 B2* | 6/2012 | Marshall et al. | 382/128 |
| 8,380,471 B2* | 2/2013 | Iannotti et al. | 703/6 |
| 2004/0013291 A1* | 1/2004 | Hillman | 382/128 |
| 2006/0025673 A1* | 2/2006 | De Leon et al. | 600/410 |
| 2009/0226055 A1* | 9/2009 | Dankowicz et al. | 382/128 |

OTHER PUBLICATIONS

Grenander and Miller, 1996, Statistical Computing and Graphics Newsletter 7, 3-8.

Beg et al., "Computing Large Deformation Metric Mappings via Geodesic Flows of Diffeomorphisms," International Journal of Computer Vision, 61, 2005 139-157.

Pruesmann et al., "SENSE: sensitivity encoding for fast MRI," Magn. Reson. Med. 42, 1999, 952-962.

Woods et al., "Automated Image Registration: I. General methods and intrasubject, intramodality validation," J. Comput. Assist. Tomogr. 22, 1988, 139-152.

Pierpaoli and Basser, "Toward a quantitative assessment of diffusion anistropyy," Magn. Reson. Med. 36, 1996, 893-906.

Alexander et al., "Spatial Transformations of Diffusion Tensor Magnetic Resonance Images," IEEE Trans. Med. Imaging 20, 2001, 1131-1139.

Xu et al., "Spatial Normalization of Diffusion Tensor Fields," Magn. Reson. Med. 50, 2002, 175-182.

Mori et al., "Stereotaxic white matter atlas based on diffusion tensor imaging in an ICBM template," Neuroimage 40, 2008, 570-582.

Jiang et al., DtiStudio: resource program for diffusion tensor computation and fiber bundle tracking. Comput. Methods Programs Biomed 2006;81(2):106-116.

Ma et al., "Bayesian Template Estimation in Computational Anatomy," Neuroimage, Aug. 2008, 42(2): 252-61.

* cited by examiner

ADVANCED COST FUNCTIONS FOR IMAGE REGISTRATION FOR AUTOMATED IMAGE ANALYSIS: MULTI-CHANNEL, HYPERTEMPLATE AND ATLAS WITH BUILT-IN VARIABILITY

CROSS-REFERENCE OF RELATED APPLICATION

This application is a U.S. National Stage Application of Application No. PCT/US2009/049812, filed Jul. 7, 2009, which claims priority to U.S. Provisional Application No. 61/134,178, filed Jun. 7, 2008, each of which is incorporated by reference in its entirety.

The U.S. Government has a paid-up license in this invention and the right in limited circumstances to require the patent owner to license others on reasonable terms as provided for by the terms of Grant No.: R01AG20012 and P41RR15241, awarded by the National Institutes of Health.

BACKGROUND

1. Field of Invention

The current invention relates to non-invasive imaging systems and methods, and more particularly to imaging systems and methods that provide automatic segmentation of tissue structures in a human or animal subject in a non-invasive manner.

2. Discussion of Related Art

Radiological diagnosis is based on qualitative and subjective judgment. Even though quantitative analyses may significantly improve our ability to detect and characterize abnormalities, currently there are essentially no quantitative techniques accepted as a part of routine radiological diagnosis. This is partly due to difficulties in analyzing tissues based on radiological imaging, such as, for example, magnetic resonance (MR) and computed tomography (CT) images. For example, high quality segmentation of the brain boundary requires a considerable amount of manual labor. Further segmentation of, for example, the brain into substructures, takes even more time. Conventional automated programs for various types of tissue identification and segmentation only provide approximate results. This means, even a very basic image analysis such as the brain volume, can not be readily obtained quickly and automatically. Therefore, there remains a need for improved non-invasive imaging systems and methods.

SUMMARY

Some embodiments of the current invention provide a non-invasive imaging system, comprising: an imaging scanner; a signal processing system in communication with the imaging scanner to receive an imaging signal from the imaging scanner; and a data storage unit in communication with the signal processing system, wherein the data storage unit stores template data corresponding to a tissue region of a subject under observation, wherein the signal processing system is adapted to compute, using the imaging signal and the template data, refined template data corresponding to the tissue region, and wherein the refined template data incorporates subpopulation variability information associated with the tissue region such that the signal processing system provides an image of the tissue region in which a substructure is automatically identified taking into account the subpopulation variability information.

Some embodiments of the current invention provide a workstation, comprising: a receiving engine to receive an imaging signal from a non-invasive imaging scanner; a normalization engine to provide, using the imaging signal and initial template data, an image of a tissue region of a subject under observation in which a substructure is automatically identified; and a construction engine to compute refined template data by incorporating subpopulation variability information associated with the tissue region.

Some embodiments of the current invention provide a method of image processing, implemented by one or more processors executing software code stored on one or more data storage devices, the method comprising: receiving initial template data corresponding to a tissue region having at least one substructure and a plurality of images showing the tissue region from at least one subject from at least one of an imaging system, the one or more data storage devices, another one or more data storage devices, a software simulation executed by the one or more processors, or a software simulation executed by another one or more processors; computing, based on the plurality of images and the initial template data, refined template data corresponding to the tissue region; and storing the refined template data on an output device, wherein the refined template data incorporates subpopulation variability information associated with the tissue region.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing the embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Figure 1:
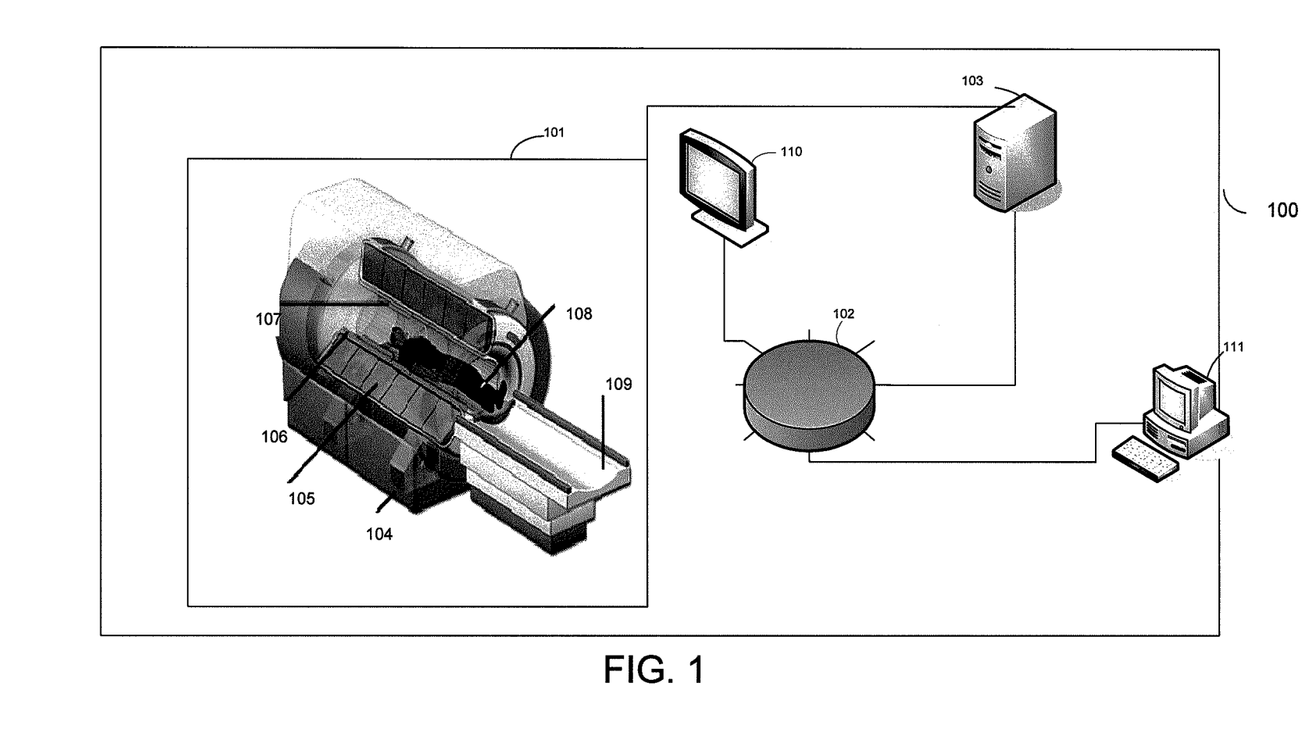
FIG. 1 is a schematic illustration of a non-invasive imaging system according to an embodiment of the current invention.

FIG. 1 is a schematic illustration of a non-invasive imaging system 100 according to some embodiments of the current invention. The non-invasive imaging system 100 includes an imaging scanner 101, a data storage unit 102, and a signal processing unit 103. Imaging scanner 101 may be, but is not limited to, a magnetic resonance imaging (MRI) scanner, a computed tomography (CT) scanner, a positron emission tomography (PET) scanner, a single positron emission computed tomography (SPECT) scanner, or combinations thereof. For example, an MRI scanner may have a base 104 to support a main magnet 105 (providing a substantially uniform main magnetic field $B_0$ for a subject 108 under observation on scanner bed 109), a gradient system 106 (providing a perturbation of the main magnetic field $B_0$ to encode spatial information of the constituent water molecules of subject 108 under observation), and a radio-frequency (RF) coil system 107 (transmitting electromagnetic waves and receiving magnetic resonance signals from subject 108).

Data storage unit 102 stores template data corresponding to a tissue region of subject 108 under observation. The tissue region may be, for example, a brain, a heart, a muscle, and other intended organ of subject 108. The term "template" used herein does not necessarily require an actual material object, such as a three dimensional material object. It will be used generally to also refer to data or information that represents a geometrical configuration. A template of the tissue region may be derived from, for example, a plurality of images from a subpopulation with similar characteristics to that of subject 108. The plurality of images may be, for example, MRI images, CT images, PET images, SPECT images, etc. For example, the images can come from the same age group as subject 108 in some applications. This is because each age range may have different tissue shapes and contrasts. For example, the human brain undergoes considerable shape and contrast changes during the first 24 months of age. During this period, templates should be created from infants within a small range of ages (e.g., 0-1 month, 1-2 months, 2-4 months, etc.). The brain also undergoes aging processes which become apparent after approximately age 60. Therefore specific templates may be required for an older subpopulation. Templates can be constructed to take into account variations between genders, races, health conditions, or other subpopulations based on the potential application. A template may incorporate information from images from at least one subject that is different from subject 108 under observation. A template may incorporate information from images from a previous scan of subject 108 under observation. For example, a template may be derived from images of a variety of different contrasts, each favorably delineating, for example, some substructures in the tissue region. For example, $T_1$-weighted magnetic resonance images suitable for the cortex and deep gray matter structures of the brain may be used. For example, $T_2$-weighted magnetic resonance images having higher contrasts for the ventricles of the brain may be used. For example, diffusion tensor images in which intra-white matter structures of the brain are best delineated may be used. The template may comprise shape information of the tissue region. The template may further incorporate variability information associated with registering the soft tissue region in the images from a subpopulation of subjects to the shape information. Registering a soft tissue region in an image from a subject to the shape information of a template may involve warping or transforming (e.g., translation, scaling, deforming, etc.) the soft tissue region in the image to align with the shape information of the template. Registering may also be referred to as normalizing. The term "template" include, but is not limited to these examples.

Data storage unit 102 may be, for example, a hard disk drive, a network area storage (NAS) device, a redundant array of independent disks (RAID), a flash drive, an optical disk, a magnetic tape, a magneto-optical disk, etc. However, the data storage unit 102 is not limited to these particular examples. It can include other existing or future developed data storage devices without departing from the scope of the current invention.

Signal processing system 103 is in communication with imaging scanner 101 to receive imaging signals for forming images of subject 108. Signal processing system 103 may be partially or totally incorporated within a structure housing imaging scanner 101. Signal processing system 103 may be at least partially incorporated in a workstation that is structurally separate from and in communication with imaging scanner 101. Signal processing system 103 may be incorporated in a workstation that is structurally separate from and in communication with imaging scanner 101. Signals received by signal processing system 103 may be associated with, for example, a magnetic resonance contrast parameter, such as, for example, a relaxation time $T_1$, a relaxation time $T_2$, an apparent diffusion coefficient, a property associated with the blood oxygenation level dependent (BOLD) effect, a property associated with the diffusion tensor, etc.

Signal processing system 103 is in communication with data storage unit 102. Signal processing system 103 is adapted to compute, from the template, a refined template corresponding to the tissue region. The refined template may incorporate variability information associated with registering the tissue region in the images from at least one subject to the refined template. The variability information may be a variability map. The images being processed by signal processing system 103 may have multiple contrasts, each favorably delineating a portion of the substructures of the tissue region. Signal processing system 103 may be adapted to register the tissue region in the images from subject 108 to the template based on the multiple contrasts. The registration results can be displayed on a viewing station 110 or a console station 111. The registration results may be used for further image analysis and disease diagnosis.

Viewing station 110 or a console station 111 may be, for example, a display device or a printing device. Example display devices may include, for example, a cathode ray tube (CRT), a light-emitting diode (LED) display, a liquid crystal display (LCD), a digital light projection (DLP) monitor, a vacuum florescent display (VFDs), a surface-conduction electron-emitter display (SED), a field emission display (FEDs), a liquid crystal on silicon (LCOS) display, etc. Example printing devices may include, for example, toner-based printers, liquid ink-jet printers, solid ink printers, dye-sublimation printers, and inkless printers such as thermal printers and ultraviolet (UV) printers, etc.

Figure 2A:
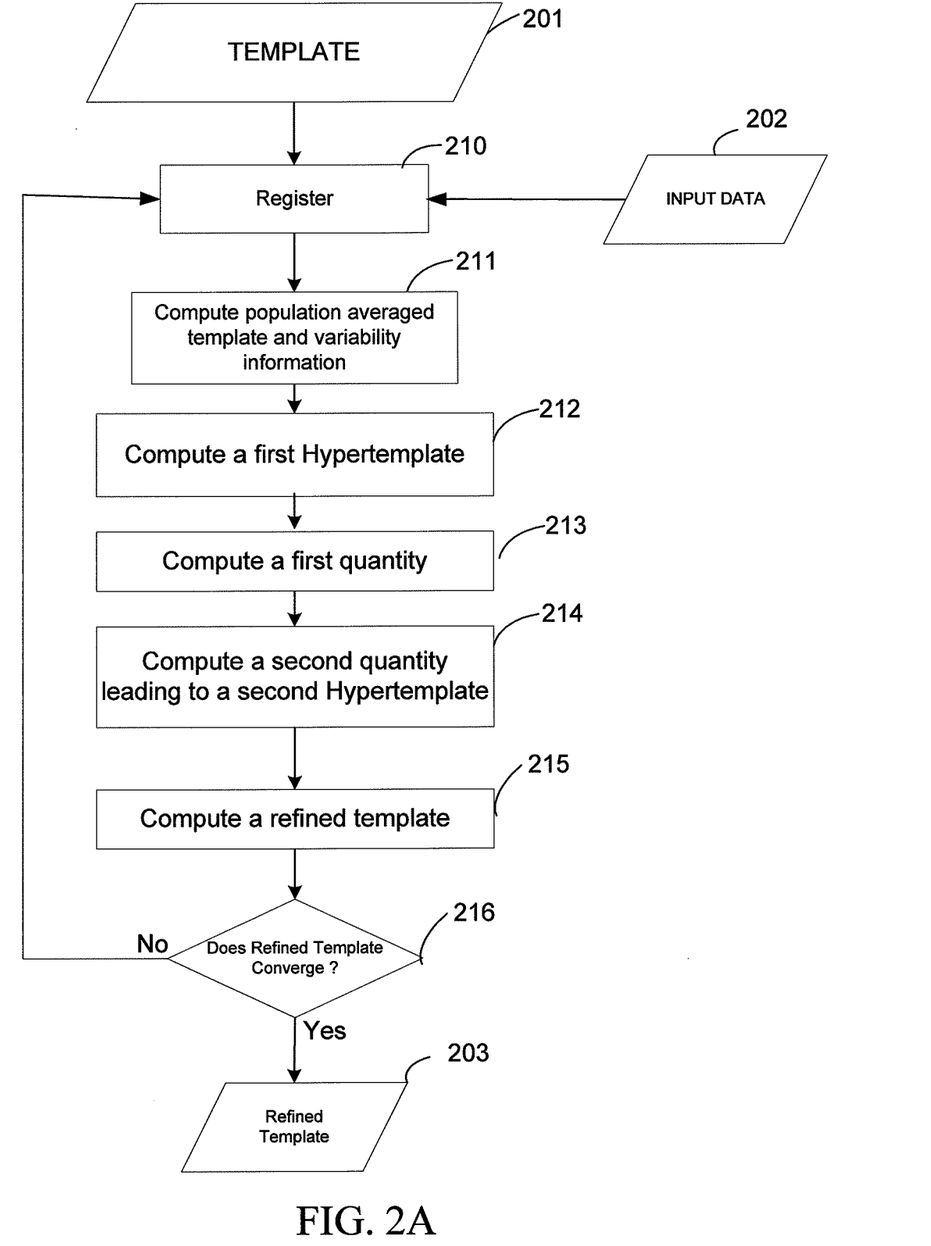
FIG. 2A shows a flow chart according to some embodiments of the current invention.

FIG. 2A shows a flow chart illustrating processes, implemented by one or more processors executing software code stored on one or more data storage devices, according to some embodiments of the current invention. The processors may be signal processors, computer processors, or combinations thereof. Example signal processors may include programmed field programmable gated array (FPGA) chips, programmed digital signal processing (DSP) chips, application specific integrated circuits (ASIC) chips, etc. Example computer processors may include single core or multi-core central processing units (CPU), single-core or multi-core graphic unit processing (GPU) chips, etc. In some embodiments of the current invention, the processes illustrated in FIG. 2A can be performed by data storage unit 102 and signal process unit 103.

Block 201 corresponds to an initial template, which can be an image from a single subject or a population-averaged image, for example. Initial template 201 corresponds to a tissue region having at least one substructure. Block 202 represents input data comprising multiple images from at least one subject. Input data 202 may be a plurality of images showing the tissue region from at least one subject from at least one of an imaging system, the one or more data storage devices, another one or more data storage devices, a software simulation executed by the one or more processors, or a software simulation executed by another one or more processors. Block 203 represents a refined template as an output of the flow chart. Refined template 203 incorporated subpopulation variability information.

In block 210, the images may be registered to initial template 201. Registration may involve warping or transforming (e.g., translation, scaling, deforming, etc.) the soft tissue region in the images to align with the shape information of initial template 201. A transformation algorithm, called Large Deformation Diffeomorphic Metric Mapping (LDDMM) (Miller et al., 1993, Proc Natl Acad Sci, 90, 1194-11948; Joshi et al., 1995, Geometric methods in Applied Imaging, San Diego, Calif.; Granander and Miller, 1996, Statistical computing and graphics newsletter 7, 3-8), may be used during the registration. There can be several important technically attractive features of LDDMM. First, LDDMM is highly non-linear and can match the shapes of two brains. It can even transform a brain with severe atrophy. Second, LDDMM can achieve topology preservation. Topology preservation may be an very important feature when applying a morphing algorithm to a biological entity. For example, when morphing one face to another, if topology is not preserved, non-biological results (e.g., two eyes become three eyes) can occur. Third the transformation can be reciprocal. It is noted that other transformation algorithms that can generate image transformation and preserve tissue topology can be used instead of LDDMM. In some cases, e.g. when only subtle changes in soft tissue regions are expected, the requirement of topology preserving can be waived.

In Block 211, all registered data may be averaged to create a population-averaged template and variability information 211. The variability information may be a population variability map that encodes the degree of anatomical variability within the population of subjects at each pixel in the template.

In block 212, the population averaged template may be used to calculate a hypertemplate as discussed below.

In the setting of diffeomorphic metric mapping, the set of anatomical shapes may be placed into a metric shape space. This may be modeled by assuming that the shape is generated one from the other via a flow of diffeomorphic solutions of ordinary differential equations $\dot{\phi}=v_t(\phi_t)$, $t\in[0,1]$ starting from the identity map $\phi_0=\text{id}$, and associated vector fields $v_t$, $t\in[0,1]$. A metric distance between target shape $I_{t\,arg}$ and template shape $I_{temp}$ may be defined, for example, as the length of the geodesic curves $\phi_t \cdot I_{temp}$, $t\in[0,1]$ through the shape space such that $\phi_1 \cdot I_{temp}=I_{t\,arg}$ at time t=1. For instance, in the image case, the group action may be taken as $\phi_1 \cdot I_{temp}=I_{temp} \circ \phi_1^{-1}$. These curves $\phi_t \cdot I_{temp}$, $t\in[0,1]$ may be generalizations of simple finite dimensional curves. The metric between two shapes $I_{temp}$ and $I_{t\,arg}$ may be determined by the integrated norm $\|v_t\|_V$ of the vector field generating the transformation, where $v_t \in V$, a smooth Hilbert space with kernel K and norm $\|\cdot\|_V$. V may be a space of smooth vector field so that solutions are diffeomorphisms. Equivalently, the metric distance may be computed through $m_t$, termed the momentum, a linear transformation of $v_t$ defined by the kernel, $K: v_t \to m_t = K^{-1} v_t$ according to $$\rho(I_{temp}, I_{target})^2 = |\inf_{v: \dot{\phi}_t=v_t \cdot \phi_t, \phi_0=id} \int_0^1 \|v_t\|_V^2 dt \text{ such that } \phi_1 \cdot I_{temp} \quad (1)$$
$$= I_{target}.$$
$$= |\inf_{m: \dot{\phi}_t=m_t \cdot \phi_t, \phi_0=id} \int_0^1 \langle m_t, Km_t\rangle dt \text{ such that } \phi_1 \cdot I_{temp}$$
$$= I_{target}.$$

The Euler equation associated with Equation (1) indicates that the momentum along the geodesic $\phi_t$ is conserved, implying the initial momentum $m_0$ encodes the geodesic connecting $I_{temp}$ and $I_{t\,arg}$ according to $$m_t = \|D\phi_t^{-1}|(D\phi_t^{-1})^* m_0 \circ \phi_t^{-1}. \quad (2)$$

This may reduce the problem of studying shapes of a population in a nonlinear diffeomorphic metric space to the problem of studying the initial momenta in a linear space. A random orbit model, as discussed below, is based on studying the initial momenta in the linear space.

Anatomical configurations $I \in \mathcal{I}$ may be defined as elements, wherein I are functions indexed over $X \subset R^3$, $I(x)$, $x \in X$. The orbit may be generated from an exemplar $I_{temp} \in \mathcal{I}$. The template is unknown and must be estimated. All elements $I \in \mathcal{I}$ are generated by the flow of diffeomorphisms from the template for some $\phi_t$, $I=\phi_1 \cdot I_{temp}$, where $\phi_t$ is an element of the space of diffeomorphisms. The task is to estimate $I_{temp}$ from a set of observed objects in I, $J^{(1)}, J^{(2)}, \ldots, J^{(n)}$.

The random model includes two parts. The first part of the random model assumes the anatomies $I^{(i)} \in \mathcal{I}$, $i=1, 2, \ldots, n$, are generated via geodesic flows of the diffeomorphism equation $\dot{\phi}_t^{(i)}=v_t(\phi_t^{(i)})=Km_t^{(i)}(\phi_t^{(i)})$, $t\in[0,1]$ from $I_{temp}$, so that the conservation equation holds and the flow satisfies the conservations of momentum Equation (2). Thus, when $m_0^{(i)}$, $i=1, \ldots, n=1, 2, \ldots$, are considered as hidden variables, the probability law on $I^{(i)} \in \mathcal{I}$ is induced via the random law on the initial momenta $m_0^{(i)}$ in a linear space, which may be modeled as independent and identically distributed Gaussian random fields (GRF) with zero mean and covariance matrix $K^{-1}/\lambda$. The second part of the random model is the observable data $J^{(i)}$, the medical images. $J^{(i)}$ may be assumed as conditional Gaussian random fields with mean fields $I^{(i)}=\phi_t^{(i)} \cdot I_{temp}$ with a variance of $\sigma^2$. The goal is to estimate the template $I_{temp}$ and $\sigma^2$ from the set of observables $J^{(1)}, J^{(2)}, \ldots, J^{(n)}$.

To obtain the unknown template, an ancillary "hypertemplate", $I_0$, may be introduced so that the template is generated from it via the flow of diffeomorphisms of $\phi_t$ such that $I_{temp}=\phi_1 \cdot I_0$. Its associated momentum may be denoted as $m_0$.

Bayesian strategy may be used to estimate the initial momentum $m_0$ from the set of observations $J^{(i)}$, $i=1, \ldots, n$ by computing the maximum a posteriori (MAP) of f $(m_0|J^{(1)}, J^{(2)}, \ldots, J^{(n)})$. To estimate f $(m_0|J^{(1)}, J^{(2)}, \ldots, J^{(n)})$, $m_0^{(i)}, \ldots, m_0^{(n)}$ associated with $\phi_0^{(i)}$, $i=1, 2, \ldots, n$ may be included as hidden variables. Thus, the log-likelihood of the complete data $(m_0, m_0^{(i)}), J^{(i)}, i=1, 2, \ldots, n)$ can be written as $$\log f(m_0, \sigma^2, m_0^{(1)}, \ldots, m^{(n)}, J^{(1)}, \ldots, J^{(n)} | I_0) = \quad (3)$$
$$-\lambda \langle m_0, K_0 m_0 \rangle - \sum_{i=1}^n \left( \langle m_0^{(i)}, Km_0^{(i)}\rangle + \frac{1}{\sigma^2} D(\phi_1^{(i)} \cdot \phi_1 \cdot I_0, J^{(i)}) + n \log \sigma^2 \right).$$

where $I_0$ is the hypertemplate; $J^{(i)}$ is the observation of i-th subject. The paired $(\phi_t, m_0)$ and $(\phi_t^{(i)}, m_0^{(i)})$ satisfy the shooting equation as specified in Equation (2) above. $K_0^{-1}$ and are covariance matrices of $m_0$ and $m_0^{(i)}$ that are known and correspond to the kernel of Hilbert space of velocity fields; $D(\phi_1^{(i)} \cdot \phi_1 \cdot I_0, J^{(i)})$ quantifies the similarity between the ith subject and deformed template $\phi_1^{(i)} \cdot \phi_1 \cdot I_0$; $\sigma^2$ is an estimate of the variance of the difference between $\phi_1^{(i)} \cdot \phi_1 \cdot I_0$ and $J^{(i)}$ among n subjects, and $D(\phi_1^{(i)} \cdot \phi_1 \cdot I_0, J^{(i)})$ may be defined according to:

$$D(\phi_1^{(j)} \cdot I_0, J^{(j)}) = \|(I_0 \circ \phi_1^{-1} \circ \phi_1^{(i)-1} - J^{(i)})w\|^2, \quad (4)$$

where w is the population variability map, as discussed above in block 211.

The expectation of the complete data log-likelihood given the old template $m_0^{old}$ and variance $\sigma^{2old}$ may be computed according to:

$$Q(m_0, \sigma^2 \mid m_0^{old}, \sigma^{2old}) = \quad (5)$$

$$E\{\log f(m_0, \sigma^2, m_0^{(1)}, \ldots, m^{(n)}, J^{(1)}, \ldots, J^{(n)} \mid I_0) \mid m_0^{old},$$

$$\sigma^{2old}, J^{(1)}, \ldots, J^{(n)}\} = -\lambda\langle m_0, K_0 m_0\rangle -$$

$$E\left\{\sum_{i=1}^n \left(\langle m_0^{(i)}, K m_0^{(i)}\rangle + \frac{1}{\sigma^2}\|(I_0 \cdot \phi_1 \cdot \phi_1^{(i)} - J^{(i)})w\|^2\right) + n\log\sigma^2 \,\middle|\, m_0^{old},\right.$$

$$\left.\sigma^{2old}, J^{(1)}, \ldots, J^{(n)}, I_0\right\}.$$

The new template may be generated by maximizing the following Q-function with respect to $m_0$, and $\sigma^2$, given the following update equation:

$$m_0^{new}, \sigma^{2new} = \operatorname{argmax}_{m_0, \sigma^2} Q(m_0, \sigma^2 \mid m_0^{old}, \sigma^{2old}) \quad (6)$$

$$= \operatorname{argmin}_{m_0, \sigma^2} -\lambda\langle m_0, K_0 m_0\rangle + \sum_{i=1}^n E$$

$$\left\{\frac{1}{\sigma^2}\|(I_0 \cdot \phi_1^{-1} \cdot \phi_1^{(i)} - J^{(i)})w\|^2 \,\middle|\, m_0^{old},\right.$$

$$\left.\sigma^{2old}, J^{(1)}, \ldots, J^{(n)}, I_0\right\} + n\log\sigma^2$$

Equation (6) takes into account that the conditional expectation of $\langle m_0^{(i)}, K m_0^{(i)}\rangle_2$ is constant.

Following Ma et al. (Ma J, Miller M I, Trouvé A, Younes L. "Bayesian template estimation in computational anatomy". Neuroimage. 2008 Aug. 1; 42(1):252-61), $\sigma^2$ and $m_0$ may be obtained by updating $\sigma^2$ using the current value of $m_0$, and then optimizing $m_0$ using the updated value of $\sigma^2$ according to the following sequence of equations:

$$\sigma^{2new} = \frac{1}{n}\sum_{i=1}^n \|(I_0 \cdot \phi_1^{-1old} \cdot \phi_1^{(i)-1} - J^{(i)})w\|^2 \quad (7)$$

$$m_0^{new} = \operatorname{argmin}_{m_0} \lambda\langle m_0, K_0 m_0\rangle + \frac{1}{\sigma^{2new}}\|(\bar{I}_0 \cdot I_0 \cdot \phi_1^{-1})\sqrt{\alpha}\|^2 \quad (8)$$

where $\bar{I}_0 = \dfrac{\sum_{i=1}^n J^{(i)} \cdot \phi_1^{(i)}|d\phi_1^{(1)}|}{\sum_{i=1}^n |d\phi_1^{(i)}|}$, and $\alpha = w^2 \sum_{i=1}^n |d\phi_1^{(i)}| \cdot |d\phi_1^{(i)}|$ is the Jacobian determinant of $\phi_1^{(i)}$. $I_0$ may be an initial instance of the hypertemplate $I_0$ and $\alpha$ is a weighting factor. The variational problem listed in Equation (8) may be referred as "modified LDDMM-image mapping" where the weight $\sqrt{\alpha}$ is introduced.

In the first iteration, $m_0=0$ may be set and the current template may be considered as the current hypertemplate. The LDDMM weighted image mapping algorithm may then be applied to register the current template to each individual subject and obtain estimates each of $m_t^{(i)}$ and $\phi_t^{(i)}$. Thus, in block 212, $\bar{I}_0$ and $\alpha$ may be computed based on $m_t^{(i)}$ and $\phi_t^{(i)}$, as discussed above. $\bar{I}_0$ may be a first hypertemplate $I_0$ (e.g., a initial instance of the hypertemplate $I_0$ in a loop of computations) and $\alpha$ is a weighting factor.

In block 213, a first quantity may be computed. The first quantity characterizes a variance of difference between the images showing the tissue region and the transformed hypertemplate $I_0$ being estimated. For example, $\sigma^2$ according to Equation (7) may be computed in block 213.

In block 214, a second quantity may be computed. The second quantity characterizes a momentum of a linear transformation from the images showing the tissue region to the hypertemplate $I_0$ being estimated. For example, $m_t$ and $\phi_t$ connecting $\bar{I}_0$ as the first hypertemplate $I_0$ to a second hypertemplate $I_0$ may be computed using a modified LDDMM-image mapping algorithm as given in Equation (7). The second hypertemplate $I_0$ may be a new instance of the hypertemplate $I_0$ being estimated in a loop of computations. The second hypertemplate $I_0$ may be estimated, for example, via the computed $m_t$ and $\phi_t$.

In block 215, a refined template may then be computed as $I_0 \circ \phi_1^{-1}$, for example, using the second hypertemplate $I_0$.

In block 216, if the refined template 203 converges (e.g., the incremental differences between successively generated refined templates 203 are insignificant for the particular application), refined template 203 generated as an output. Otherwise, flow may go to block 210 and the computations between block 210 and block 215 may be repeated, by applying the refined template 203 to the input data 202. After each iteration, the refined template 203 may move closer to the center of the metric space.

Using the refined template 203 generated according to some embodiments of the current invention, new analysis such as pixel-based or atlas-based analysis may be performed. The analysis may include automated identification of anatomical regions or pixels and automated tissue segmentation.

Figure 2B:
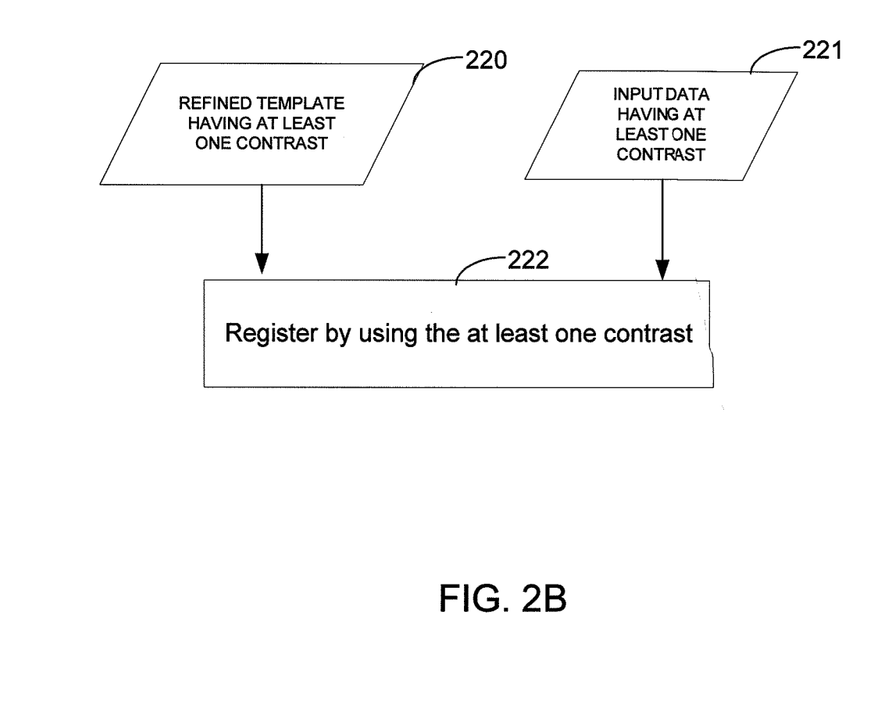
FIG. 2B shows another flow chart according to some embodiments of the current invention.

FIG. 2B shows a flow chart according to some embodiments of the current invention. In block 222, input data 221 having at least one contrast may be registered to refined template 220 having at least one contrast.

The registration using multiple contrasts may be performed in many ways. For example, a Large Deformation Diffeomorphic Mapping (LDDMM) may be used. The deformable template model of Granander (Granander and Miller, 1996, Statistical computing and graphics newsletter 7, 3-8) models the observed anatomical images, I, as an orbit under the group of transformations, G, acting on a template image, $I_0$, according to $I=GI_0=\{I_0\circ\phi^{-1}, \phi\in G\}$. Utilizing this model, for two given images, $I_0, I_1: \Omega \subset R^3 \to R$, the LDDMM algorithm (Beg, M. F., Variational and computational methods for flows of diffeomorphisms in image matching and growth in computational anatomy. PhD thesis. The Johns Hopkins University, July 2003; Beg et al., International Journal of Computer Vision, 61, 139-157, 2005) may be used to calculate the diffeomorphic transformation, $\phi:\Omega\to\Omega$, by registering the images such that $I_1=I_0\circ\phi^{-1}$. $\Omega \subseteq R^3$ is the 3D cube on which the data is defined. The optimal transformation, $\phi$, may be generated as the end point, $\phi=\phi_1^v$, of the flow of smooth time-dependent vector field, $v_t \in V$, $t\in[0,1]$, with the ordinary differential equation, $$\frac{d\phi_t^v}{dt} = v_t(\phi_t^v), t \in [0, 1], \quad (9)$$

where $\phi_0$ is the identity transformation such that $\phi_0(x)=x$, $x\in\Omega$. V is the space of smooth compactly supported vector fields. Then, the optimal transformation, $\hat{\phi}$, may be calculated by integrating the vector field that is found by minimizing the following equation.

$$\hat{v} = \underset{v:d\phi_t^v/dt=v_t(\phi_t^v)}{\operatorname{argmin}} \left( \int_0^1 \|v_t\|_V^2 \, dt + \frac{1}{\sigma^2} \|I_0 \cdot \varphi^{-1} - I_1\|_{L^2}^2 \right) \quad (10)$$

In Equation (10), the minimization is with respect to the vector field v satisfying the constraint specified in Equation (9). After the minimization is completed, the optimal transformation, $\hat{\phi}$, may be calculated from Equation (9) by integration.

Since smoothness on the vector fields, $v \in V$ may be enforced, the solution to Equation (10) may be in the space of diffeomorphisms. The smoothness enforcement may be achieved by defining the norm on V as $\|f\|_V = \|Lf\|_{L^2}$. L is a differential operator defined as:

$$L = -\alpha \nabla^2 + \gamma I_{3 \times 3}, \quad (11)$$

where $I_{3 \times 3}$ is the identity operator and $\nabla^2$ is the Laplacian operator. $\|\cdot\|_{L^2}$ is the $L^2$ norm for the square integrable functions defined on $\Omega$. The gradient of the cost in Equation (10) is:

$$\nabla_v E_t = 2v_t - K\left( \frac{2}{\sigma^2} |D\phi_{t,1}^v| \nabla J_t^0 (J_t^0 - J_t^1) \right), \quad (12)$$

where the notation $\phi_{s,t} = \phi_s \circ \phi_t^{-1}$ is used. In Equation (12), $J_t^0 = I_0 \circ \phi_{t,0}$ and $J_t^1 = I_1 \circ \phi_{t,1}$. |Df| is the determinant of the Jacobian matrix. $K: L_2(\Omega, R^3) \to V$ is a compact self-adjoint operator, defined by $\langle a, b \rangle_{L^2} = \langle Ka, b \rangle_V$, which satisfies K (L$^{554}$L)g=g for any smooth vector field g∈V. The parameter σ provides weighting between data matching and smoothness regularization terms. In the LDDMM algorithm, Equation (10) may be solved with a gradient descent algorithm using Equation (12). In Equation (12), the effect of the operator, $K = (L^\dagger L)^{-1}$, may be low-pass filtering. The parameters α and γ may define the magnitude and frequency response of this filter For two given vector valued images, $I_0 = [I_{01}, I_{02}, \ldots, I_{0C}]$ and $I_1 = [I_{11}, I_{12}, \ldots, I_{1C}]$ with $I_{0c}, I_{1c}: \Omega \subset R^3 \to R$, c=1, ..., C, the diffeomorphic transformation, $\phi$, registering these two images, such that $I_1 = I_0 \circ \phi^{-1}$ or $[I_{11}, I_{12}, \ldots, I_{1C}] = [I_{01} \circ \phi^-, I_{02} \circ \phi^{-1}, \ldots, I_{0C} \circ \phi^{-1}]$, may be assumed to be generated as the end point of the flow of the smooth time-dependent vector field, $v_t \in V$, with the ordinary differential equation, $\partial \phi_t^v / \partial t = v_t (\phi_t^v)$, t∈[0,1]. The optimal transformation, $\hat{\phi}$ may be calculated by integrating the vector field, which is found by minimizing the following equation.

$$\hat{v} = \underset{v:d\phi_t^v/dt=v_t(\phi_t^v)}{\operatorname{argmin}} \left( \int_0^1 \|v_t\|_V^2 \, dt + \sum_{c=1}^C \left\{ \frac{1}{\sigma_c^2} \|I_{0c} \cdot \varphi^{-1} - I_{1c}\|_{L^2}^2 \right\} \right) \quad (13)$$

The index c denotes a contrast index and C denotes the total number of different contrasts. Again because the smoothness on the vector fields $v \in V$ may be enforced, the solution for Equation (13) may be in the space of diffeomorphisms. The gradient descent algorithm can be used to solve this equation. The gradient of the cost in Equation (13) may be expressed as:

$$\nabla_v E_t = 2v_t - \sum_{i=1}^N \left( K\left( \frac{2}{\sigma_c^2} |D\phi_{t,1}^v| \nabla J_t^{0c} (J_t^{0c} - J_t^{1c}) \right) \right), \quad (14)$$

$$c = 1, \ldots, C.$$

In this equation, the parameters, $\sigma_c$ (c=1, ..., C), control the weighting of contrast-matching terms and smoothness regularization terms. $J_t^{0c} = I_{0c} \circ \phi_{t,0}$ and $J_t^{1c} = I_{1c} \circ \phi_{t,0}$. |Df| is the determinant of the Jacobian matrix. $K: L_2(\Omega, R^3) \to V$ is a compact self-adjoint operator, defined by $\langle a, b \rangle_{L^2} = \langle Ka, b \rangle_V$, which satisfies $K(L^\dagger L)g = g$ for any smooth vector field g∈V.

In template estimation equations, the number of contrasts in each image may not be specified. However, if the hyper-template and the observation images are vector valued images as discussed above for images having more than one contrast information, multiple contrast images can be directly incorporated for the template estimation.

Diffusion tensor imaging (DTI) data from thirteen Alzheimer's disease (AD) patients and eighteen normal adult control subjects were used in a study, following Institutional Review Board (IRB) approval and written, informed consents gathered from the subjects. A 3.0 T MR unit (Gyroscan NT, Philips Medical Systems) was used. DTI data were acquired with a single-shot echo-planar imaging (EPI) sequence with sensitivity encoding (SENSE), using a parallel imaging factor of 2.5 (Pruessmann et al., 1999 SENSE: sensitivity encoding for fast MRI. Magn Reson Med 42, 952-962). The imaging matrix was 96×96 with a field-of-view (FOV) of 112×112 mm (normal resolution, 2.2 mm), zero-filled to 256×256 pixels. Transverse sections of 2.2 mm thickness were acquired parallel to the anterior commisure-posterior commissure line (AC-PC). A total of 55-60 sections covered the entire hemisphere and brainstem without gaps. Diffusion weighting was encoded along 32 independent orientations, and the b-value was 700 mm²/s. Five additional images with minimal diffusion weighting (b≈33 mm²/s) were also acquired (herein after $b_0$ images). The scanning time per data set was approximately 4.5 minutes. The DTI datasets were transferred to a personal computer running a Windows platform and were processed using DtiStudio (Jiang reference). Images were first aligned using Automatic Imaging Registration (Woods et al., 1998. Automated image registration: I. General methods and intrasubject, intramodality validation. J Comput Assist Tomogr 22, 139-152.) using the first minimally diffusion-weighted images as a template, to remove any potential small bulk motion that may have occurred during the scans. The six elements of the diffusion tensor were calculated for each pixel using multi-variant linear fitting. After diagonalization, three eigenvalues and eigenvectors were obtained. For the anisotropy map, fractional anisotropy (FA) was used (Pierpaoli and Basser, 1996. Toward a quantitative assessment of diffusion anisotropy. Magn. Reson. Med. 36, 893-906.). The eigenvector associated with the largest eigenvalue was used as an indicator of the fiber orientation.

A program called Landmaker was used to perform both linear and LDDMM transformations for the DTI dataset. A single subject white matter template, called the JHU-DTI-II template, was used. The template contains $T_1$, $T_2$, and DTI-derived contrasts and is linearly normalized to the international consortium of brain mapping ICBM-152 template coordinate. The template has a matrix size of 181×217×181.

During initial linear transformation, the least diffusion-weighted images ($b_0$ images) were used. The images were registered to the template using a 12-mode affine transformation of AIR. This process took less than 1 minute with 2-3 GHz xeon processors. The transformation matrix was then applied to the calculated diffusion tensor field, based on a method disclosed by Alexander and Gee (Alexander et al., 2001, IEEE Trans Med imaging 20, 1131-1139) and Xu et al (Xu et al., 2002, Magn Reson Med, 50, 175-182). The entire normalization process was performed by Landmarker and took less than 30 minutes.

After linear transformation, the registered images were re-sampled to a size of 96×128×96 with an isotropic 2 mm voxel resolution before LDDMM was applied. The LDDMM computation may require 4 to 8 GB of memory and approximately 5 hours of computation time on a cluster computer having 32 CPUs.

For each of the thirteen Alzheimer's disease patients and eighteen control subjects, the following strategies were used for image registration, namely, using only the $b_0$ images in a single-channel LDDMM with the transformations of $\phi_i^{b0}$, i=1, ..., 31; using only the FA images in a single-channel LDDMM with the transformations of $\phi_i^{FA}$, i=1, ..., 31; using both the $b_0$ images and the FA images in a multi-channel LDDMM with the transformations of $\phi_i^{B0-FA}$, i=1, ..., 31.

Figure 3A:
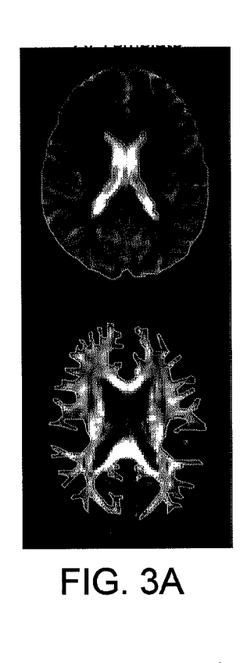
FIGS. 3A-3E provide an example of results according to some embodiments of the current invention.
Figure 3B:
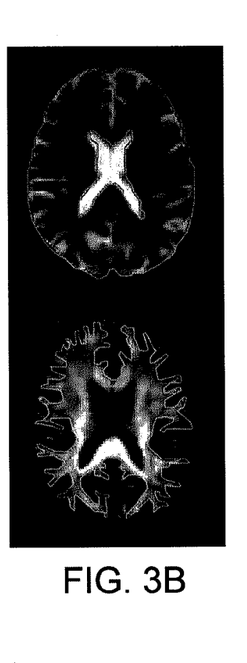
Figure 3C:
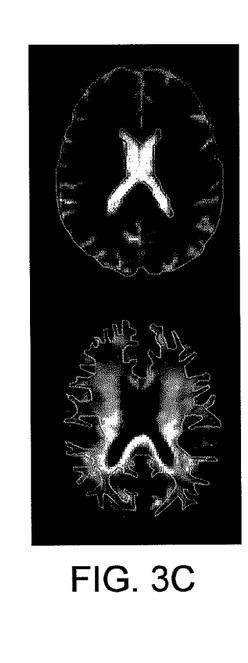
Figure 3D:
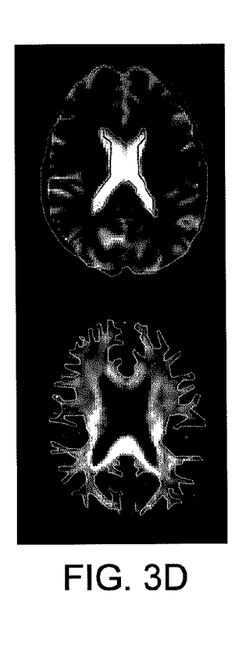
Figure 3E:
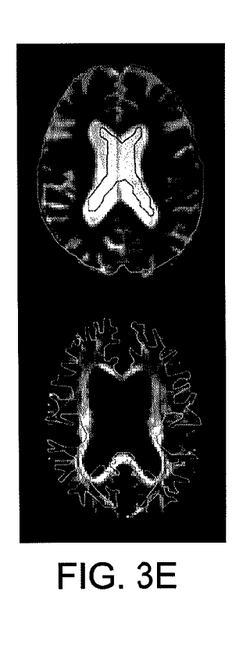

FIGS. 3A-3E shows example results from the study using some embodiments of the current invention. FIG. 3A shows the template superimposed on the brain image of a normal subject (top) and the brain image of a AD patient (bottom). FIG. 3B shows the registered images of a normal subject (top) and an AD patient (bottom) using equal weighting for FA and $b_0$ images. FIG. 3C shows the registered images of a normal subject (top) and an AD patient (bottom) using $b_0$ images only. FIG. 3D shows the registered images of a normal subject (top) and an AD patient (bottom) using FA images only. FIG. 3E shows the refined template, after incorporating both the FA and $b_0$ images, superimposed on a normal subject (top) and an AD patient (bottom).

To measure the image registration quality improvement, two types of measurements of quality can be performed, namely, a landmark-based measurement and a surface-based measurement.

According to the landmark-based measurement, landmarks for target structures can be placed in both the template and the registered images and the degree of matching of these target structures between the template and the registered images can then be measured. For example, a standard landmark set including 237 landmarks at easy-to-identify white matter structures in the JHU-DTI-II template (Mori, S., Oishi, K., Jiang, H., Jiang, L., Li, X., Akhter, K., Hua, K., Faria, A. V., Mahmood, A., Woods, R., Toga, A. W., Pike, G. B., Neto, P. R., Evans, A., Zhang, J., Huang, H., Miller, M. I., van Zijl, P., Mazziotta, J., Stereotaxic white matter atlas based on diffusion tensor imaging in an ICBM template. Neuroimage 40, 570-582, 2008) may be used. For example, the standard set of 237 white matter landmarks may be placed on the template and, for example, the FA image of each subject (total of 31) after the initial linear normalization. The FA image of each subject may be registered to the template image space using the calculated transformations $\phi_i^{b0}$, $\phi_i^{FA}$, $\phi_i^{b0-FA}$, i=1, ..., 31. The registration may involve warping or transforming (e.g., translating, scaling, and deforming) the FA image to align with the shape information of the tissue region in the template. The geometric Euclidian distances (i.e., the error distances) between the 237 white matter landmarks in the template and in the registered images may be calculated. The error distances may be averaged for the population of normal control subjects and AD patients for each transformation strategy. For example, for the normal control subjects (young adults), registration error for the results of the study using the FA images (example results shown in FIGS. 3A-3E) improved from 4.5 mm to 2.2 mm for 90% of the 237 white matter landmarks. For example, for the AD patients, registration error for the results of the study using the FA images (example results also shown in FIGS. 3A-3E) improved from 6.8 mm to 2.6 mm for 90% of the 237 white matter landmarks. These improvements are statistically significant for registration quality. Similar results were obtained using both the FA and $b_0$ images. However, using the $b_0$ images alone, no statistically significant registration improvement were observed.

The landmark-based measurement may be effective to measure registration quality improvement of the white matter. However, this measurement may be difficult for measuring registration quality improvement of the brain surface for lack of easy-to-identify landmarks in the cortex. According to the surface-based measurement, the outer brain surfaces may be defined by triangular meshes on the template and on, for example, the $b_0$ image from each subject. Surfaces may be created by thresholding. Morphological operations for removing holes from the surfaces and smoothing. Each surface may be represented as a set of vertex coordinates of the constituent triangular meshes. Defined by the set of vertices, the brain surface of each subject may be registered to the template using the calculated transformations $\phi_i^{b0}$, $\phi_i^{FA}$, $\phi_i^{b0-FA}$, i=1, ..., 31. The geometric Euclidian distances (i.e., the error distances) between the set of vertices on the template and in the registered images may be calculated. The error distances may be averaged for the population of normal control subjects and AD patients for each transformation strategy. The results show significant improvement obtained using the $b_0$ images alone or both the $b_0$ or FA images. However, using the FA images alone, no statistically significant registration improvement were observed.

Figure 4A:
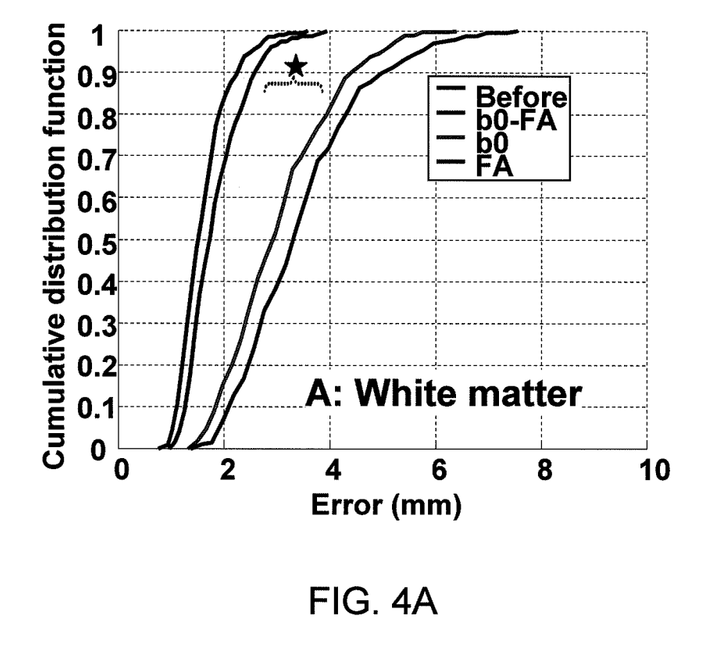
FIGS. 4A-4B show quantitative results demonstrating improvement of registration quality according to some embodiments of the current invention.
Figure 4B:
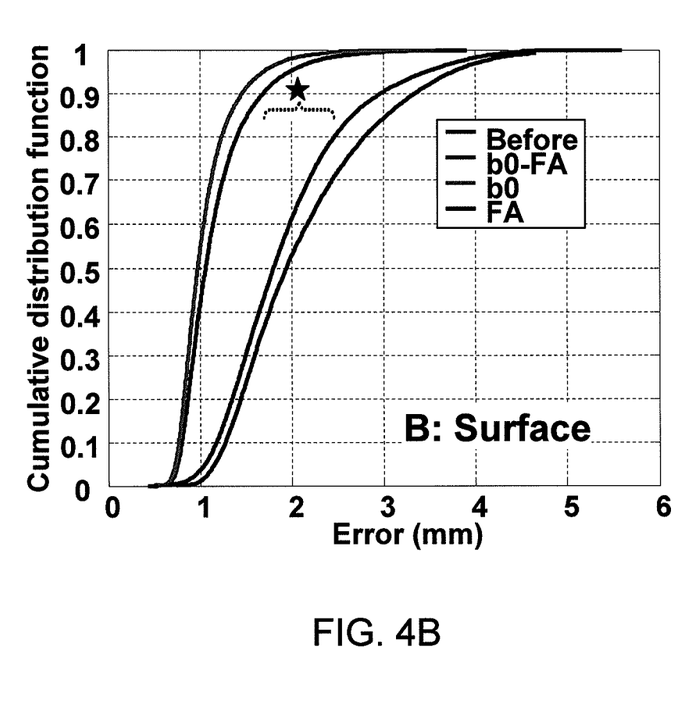

FIGS. 4A-4B show quantitative results demonstrating improvement of registration quality according to some embodiments of the current invention. FIG. 4A shows the measured cumulative distribution as a function of measured error distances between the 237 white matter landmarks in the template and in the registered images. The four curves represent results from using linear (affine) normalization only, using FA contrast only, using $b_0$, images only, and using both FA and $b_0$ images. FIG. 4B shows the same four curves measured for the quality of brain surface registration. As can be seen, the registration quality was significantly better when the both contrasts were used simultaneously.

Figure 5:
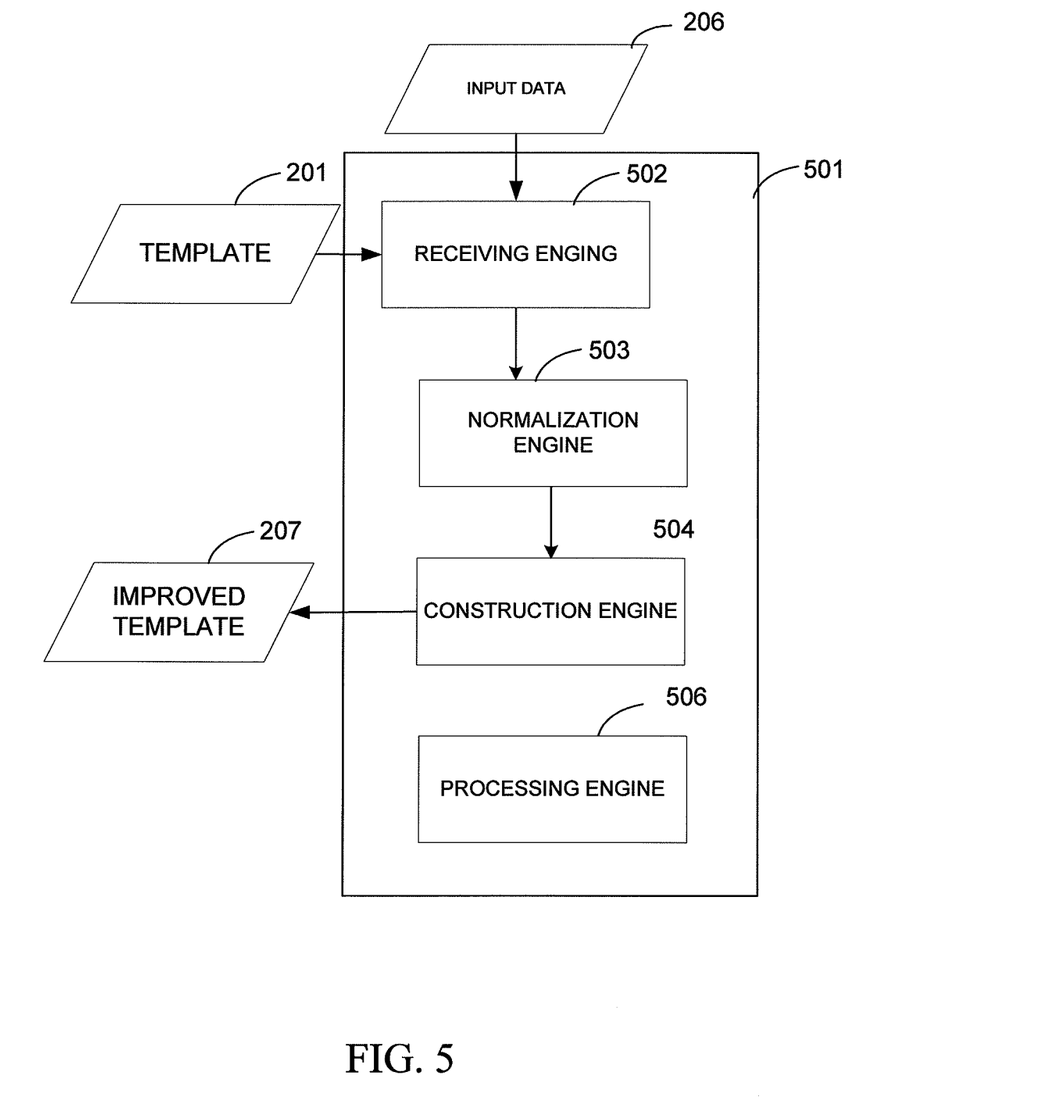
FIG. 5 shows a workstation according to some embodiments of the current invention.

FIG. 5 is a schematic illustration of a workstation 501 according an embodiment of the current invention. The workstation may include a receiving engine 502; a normalization engine 503; and a construction engine 504.

Receiving engine 502 may receive at least one image showing a tissue region from at least one subject having at least one substructure and an initial template corresponding to the tissue region. Normalization engine 503 may register the tissue region in the at least one image to the initial template. Normalization engine 503 may be constructed to implement at least one transformation using an algorithm of Large Deformation Diffeomorphic Metric Mapping (LDDMM). Construction engine 504 may construct an improved template by computing a refined template based on the at least one image and the initial template. The refined template incorporates variability information associated with registering the tissue region from the at least one subject to the refined template.

The received images have at least one contrast type that favorably delineates at least some of the substructure of the tissue region. The workstation 501 may further include a processing engine 506 to register, using the at least one contrast type, the tissue region in the received images to the refined template. The workstation 501 may also include a visualization engine to display the registered at least one image showing the tissue region. A visualization engine may be, for example, a display device or a printing device. Example display devices may include, for example, a cathode ray tube (CRT), a light-emitting diode (LED) display, a liquid crystal display (LCD), a digital light projection (DLP) monitor, a vacuum florescent display (VFDs), a surface-conduction electron-emitter display (SED), a field emission display (FEDs), a liquid crystal on silicon (LCOS) display, etc. Example printing devices may include, for example, toner-based printers, liquid ink-jet printers, solid ink printers, dye-sublimation printers, and inkless printers such as thermal printers and ultraviolet (UV) printers, etc.

Workstation 501 may be a computer with at least one central processing unit (CPU) and a plurality of memories. Workstation 501 may also be a dedicated processing machine with such devices as, for example, a field programmable gated array (FPGA), a digital signal processing (DSP) chip, a graphic processing unit (GPU), an application specific integrated circuit (ASIC), etc. Workstation 501 may also be incorporated in the imaging system 100.

The engines may be implemented by a computer with at least one processor and a plurality of memories. The processor may be, for example, one or more single-core or multi-core central processing unit (CPU), one or more single-core or multi-core graphic processing unit (GPU), etc. The computer may be a distributed computer comprising more than one processor connected via a network to divide the computation. Example networks may include, but is not limited to, an intranet, an extranet, the internet, or combinations thereof. Receiving engine 502, normalization engine 503, construction engine 504, and processing engine 506 may be implemented by, for example, a field programmable gated array (FPGA), a digital signal processing (DSP) chip, a graphic processing unit (GPU), an application specific integrated circuit (ASIC), etc.

In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A non-invasive imaging system, comprising:
an imaging scanner;
a signal processing system in communication with said imaging scanner to receive an imaging signal from said imaging scanner; and
a data storage unit in communication with said signal processing system, wherein said data storage unit stores template data corresponding to a tissue region of a subject under observation,
wherein said signal processing system is adapted to compute, using said imaging signal and said template data, refined template data corresponding to said tissue region, and
wherein the refined template data incorporates subpopulation variability information associated with said tissue region such that said signal processing system provides an image of said tissue region in which a substructure is automatically identified taking into account said subpopulation variability information.

2. The method according to claim 1, wherein said tissue region is at least one of a brain, a heart, a liver, or other intended organ of said subject under observation.

3. The imaging system according to claim 1, wherein said template data incorporates information from an image from a subject that is different from said subject under observation.

4. The imaging system according to claim 1, wherein said template data incorporates information from an image from a previous scan of said subject under observation.

5. The imaging system according to claim 1, wherein said imaging scanner is a magnetic resonance imaging (MRI) scanner, a computed tomography (CT) imaging scanner, a positron emission tomography (PET) imaging scanner, a single positron emission computed tomography (SPECT) imaging scanner, or a combination thereof.

6. The imaging system according to claim 1, wherein said imaging signal has at least one contrast type that favorably delineates at least a portion of said substructure of said tissue region.

7. The imaging system according to claim 6, wherein said at least one contrast types is taken into account when said signal processing system provides an image of said tissue region in which said substructure is automatically identified.

8. The imaging system according to claim 1, wherein said signal processing system is at least partially incorporated in a workstation that is structurally separate and in communication with said imaging scanner.

9. The imaging system according to claim 1, wherein said signal processing system is at least partially incorporated within a structure housing said imaging scanner.

10. The imaging system according to claim 1, wherein said signal processing system is adapted to compute said refined template data by maximizing a posteriori a likelihood of said imaging signal being observed, wherein said likelihood is contingent on said refined template.

11. The imaging system according to claim 10, wherein said maximizing a posteriori likelihood comprises:
computing a first hypertemplate that characterizes a center of variability of said imaging signals; and
computing, based on said first hypertemplate, a first quantity characterizing a variance of difference between said imaging signal showing said tissue region and said hypertemplate transformed to align with said imaging signal.

12. The imaging system according to claim 11, wherein said first quantity further includes contributions from a population variability map associated with said subject under observation.

13. The imaging system according to claim 11, further comprising:
computing, based on said first quantity and said first hypertemplate, a second quantify that characterizes a momentum of a linear transformation from said imaging signal to a second hypertemplate.

14. The imaging system according to claim 11, wherein said first hypertemplate is expressed as:

$$I_0 = \frac{\sum_{i=1}^{n} J^{(i)} \cdot \phi_1^{(i)} |d\phi_1^{(i)}|}{\sum_{i=1}^{n} |d\phi_1^{(i)}|};$$

said first quantity is expressed as:

$$\sigma^{2new} = \frac{1}{n}\sum_{i=1}^{n}\|(I_0 \cdot \phi_1^{-1old} \cdot \phi_1^{(i)-1} - J^{(i)})w\|^2;$$

and said second quantity is expressed as:

$$m_0^{new} = \operatorname{argmin}_{m_0} \lambda \langle m_0, K_0 m_0 \rangle + \frac{1}{\sigma^{2new}}\|(\bar{I}_0 - I_0 \cdot \phi_1^{-1})\sqrt{\alpha}\|^2,$$

wherein $J^{(i)}$ is an image observed for a i-th subject of said at least one subject, $\phi_1^{(i)}$ is a diffeomorphic transformation, w is a population variability map, $K_0^{-1}$ is a covariance matrix of $m_0$, and $\alpha = w^2 \Sigma_{i=1}^{n} |d\phi_1^{(i)}|$.

15. A workstation, comprising:
a receiving engine to receive an imaging signal from a non-invasive imaging scanner;
a normalization engine to provide, using said imaging signal and initial template data, an image of a tissue region of a subject under observation in which a substructure is automatically identified; and
a construction engine to compute refined template data by incorporating subpopulation variability information associated with said tissue region.

16. The workstation according to claim 15, wherein said imaging signal has at least one contrast type that favorably delineates at least a portion of said substructure of said tissue region.

17. The workstation according to claim 16, further comprising a processing engine to provide, by taking into account of said at least one contrast type, an image of said tissue region of said subject under observation in which said substructure is automatically identified.

18. The workstation of claim 16, further comprising:
a visualization engine to display said image of said tissue region of said subject under observation in which said substructure is automatically identified.

19. The workstation according to claim 15, wherein said normalization engine is constructed to implement at least one transformation using an algorithm of Large Deformation Diffeomorphic Metric Mapping (LDDMM).

20. A method of image processing, implemented by one or more processors executing software code stored on one or more data storage devices, comprising:
receiving initial template data corresponding to a tissue region having at least one substructure and a plurality of images showing said tissue region from at least one subject from at least one of an imaging system, the one or more data storage devices, another one or more data storage devices, a software simulation executed by the one or more processors, or a software simulation executed by another one or more processors;
computing, based on said plurality of images and said initial template data, refined template data corresponding to said tissue region; and
storing said refined template data on an output device,
wherein said refined template data incorporates subpopulation variability information associated with said tissue region.

21. The method according to claim 20, wherein said variability information is a population variability map calculated by characterizing a variance of registering said tissue region from said at least one subject to the initial template.

22. The workstation according to claim 21, further comprising registering, using the at least one contrast, said plurality of images of said tissue region to said refined template.

23. The workstation according to claim 20, wherein said plurality of images have at least one contrast type, each favorably delineating at least a portion of said at least one substructure of said tissue region.

24. The method according to claim 20, wherein said plurality of images comprise at one a magnetic resonance (MR) image, a computed tomography (CT) image, a positron emission tomography (PET) image, a single positron emission computed tomography (SPECT) image, or a combination thereof.

25. The method according to claim 20, wherein said computing a refined template is achieved by maximizing a posteriori a likelihood of said plurality of images being observed, wherein said likelihood is contingent on said refined template.

26. The method according to claim 25, wherein said maximizing a posteriori a likelihood comprises:
computing a first hypertemplate that characterizes a center of variability of said plurality of images; and
computing, based on said first hypertemplate, a first quantity characterizing a variance of difference between said plurality of images showing said tissue region and said hypertemplate transformed to align with said plurality of images.

27. The method according to claim 26, wherein said first quantity further includes contributions from a population variability map associated with said at least one subject.

28. The method according to claim 26, further comprising:
computing, based on said first quantity and said first hypertemplate, a second quantify that characterizes a momentum of a linear transformation from said plurality of images to a second hypertemplate.

29. The method according to claim 26, wherein
said first hypertemplate is expressed as:

$$\bar{I}_0 = \frac{\sum_{i=1}^{n} J^{(i)} \cdot \phi_1^{(i)} |d\phi_1^{(i)}|}{\sum_{i=1}^{n} |d\phi_1^{(i)}|};$$

said first quantity is expressed as:

$$\sigma^{2new} = \frac{1}{n}\sum_{i=1}^{n}\|(I_0 \cdot \phi_1^{-1old} \cdot \phi_1^{(i)-1} - J^{(i)})w\|^2;$$

and said second quantity is expressed as:

$$m_0^{new} = \operatorname{argmin}_{m_0} \lambda \langle m_0, K_0 m_0 \rangle + \frac{1}{\sigma^{2new}}\|(\bar{I}_0 - I_0 \cdot \phi_1^{-1})\sqrt{\alpha}\|^2,$$

wherein $J^{(i)}$ is an image observed for a i-th subject of said at least one subject, $\phi_0^{(i)}$ is a diffeomorphic transformation, w is a population variability map, $K_0^{-1}$ is a covariance matrix of $m_0$, and $\alpha = w^2 \Sigma_{i=1}^{n} |d\phi_1^{(i)}|$.

30. The method of claim 20, wherein said refined template data is computed from said second hypertemplate.

31. A computer readable medium to store software, which software when executed by a computer, causes the computer to perform the method according to claim 20.

* * * * *